United States Patent [19]

Jacobsen et al.

[11] Patent Number: 5,783,512
[45] Date of Patent: Jul. 21, 1998

[54] CATALYST COMPONENT DISPERSION COMPRISING AN IONIC COMPOUND AND SOLID ADDITION POLYMERIZATION CATALYSTS CONTAINING THE SAME

[75] Inventors: Grant B. Jacobsen, Houston, Tex.; Theo J. P. Stevens, Dwarsstraat; Pierre H. H. Loix, Langenakkerstraat, both of Belgium

[73] Assignee: The Dow Chemical Company, Midland, Mich.

[21] Appl. No.: 768,518

[22] Filed: Dec. 18, 1996

[51] Int. Cl.⁶ .................................. C08F 4/645
[52] U.S. Cl. ................ 502/124; 502/150; 502/152; 502/155; 502/156; 502/158; 502/167; 502/103; 502/117; 502/118; 502/125; 502/108; 526/127; 526/133; 526/352; 526/352.2; 526/943
[58] Field of Search ................... 502/150, 152, 502/155, 156, 158, 167, 103, 117, 118, 124, 125

[56] References Cited

FOREIGN PATENT DOCUMENTS

| | | |
|---|---|---|
| 0 418 044 A2 | 3/1991 | European Pat. Off. |
| 0 327 649 B1 | 7/1992 | European Pat. Off. |
| 0 522 581 A1 | 1/1993 | European Pat. Off. |
| 0 725 086 A2 | 8/1996 | European Pat. Off. |
| 0 727 443 A1 | 8/1996 | European Pat. Off. |
| WO 91/09882 | 7/1991 | WIPO |
| WO 93/11172 | 6/1993 | WIPO |
| WO 93/21238 | 10/1993 | WIPO |
| WO 94/03506 | 2/1994 | WIPO |
| WO 94/03509 | 2/1994 | WIPO |
| WO 94/07927 | 4/1994 | WIPO |
| WO 96/04319 | 2/1996 | WIPO |
| WO 96/28480 | 9/1996 | WIPO |

*Primary Examiner*—Mark Nagumo
*Attorney, Agent, or Firm*—John H. Roberts

[57] ABSTRACT

A non-supported solid catalyst comprising (a) an ionic compound comprising a.1) a cation and a.2) an anion having up to 100 nonhydrogen atoms and said anion containing at least one substituent comprising an active hydrogen moiety, (b) a transition metal compound, and (c) an organometal compound wherein the metal is selected from the Groups 1–14 of the Periodic Table of the Elements; a supported solid catalyst comprising (a), (b), (c), and (d) a support material, obtainable by combining components (a), (b), (c), and (d) in any order, and wherein during at least one step in the preparation of the solid catalyst, component (a) dissolved in a diluent in which (a) is soluble, is converted into solid form; a method for preparing the solid catalysts; and a process of polymerization using these solid catalysts.

49 Claims, No Drawings

CATALYST COMPONENT DISPERSION COMPRISING AN IONIC COMPOUND AND SOLID ADDITION POLYMERIZATION CATALYSTS CONTAINING THE SAME

FIELD OF THE INVENTION

This invention relates to a catalyst component dispersion comprising an ionic compound in solid form, to a non-supported solid catalyst comprising a transition metal compound, an ionic compound, and an organometal compound, to a supported solid catalyst comprising a transition metal compound, an ionic compound, an organometal compound, and a support material, to a method for preparing the catalyst component dispersion, to a method for preparing the solid catalysts, to a method for activating a catalyst suitable for addition polymerization, and to an addition polymerization process using the solid catalysts.

BACKGROUND OF THE INVENTION

Homogeneous ionic transition metal catalysts are known for their high catalytic activity in addition polymerizations, especially those of olefins and diolefins, and are capable of providing olefinic polymers of narrow molecular weight distributions and, for example when ethylene is copolymerized with a further alpha-olefin, narrow comonomer distributions. Under polymerization conditions where polymer is formed as solid particles, e.g. in gas phase or slurry phase polymerizations, these homogeneous (soluble) catalysts form polymer deposits on reactor walls and stirrers which deposits should be removed frequently as they prevent an efficient heat-exchange necessary for cooling the reactor contents, prevent the regular or continuous removal of polymer from the reactor, and cause excessive wear of the moving parts in the reactor. The polymers produced by these soluble catalysts further have undesirable particle characteristics such as a low bulk density which limits the commercial utility of both the polymer and the process. Therefore, there is a need to provide catalysts that would overcome such problems.

Several supported catalysts have been proposed for use in particle forming polymerization processes. Support materials in the prior art are typically employed in combination with catalytic components to obtain the formation of polymer particles of desirable particle size and morphology. Secondly, support materials are used to increase catalytic activity per unit of active components by depositing such components on a support material having a relatively high surface area. Furthermore, support materials are employed for anchoring thereon the catalytic components to avoid the presence of significant amounts of catalyst which under particle forming polymerization conditions becomes solubilized and gives rise to particles of undesired size and morphology, said particles contributing to the formation of polymer deposits at reactor walls and other moving parts in the reactor.

EP-327649 and EP-725086 describe solid catalysts using alumoxanes as cocatalyst. EP-327649 relates to a non-supported olefin polymerization catalyst composed of a transition metal compound and an alumoxane having an average particle size of 5 to 200 micrometers and a specific surface area of 20 to 1,000 m$^2$/g. EP-725086 describes a solid component of a catalyst for ethylene and alpha-olefins (co)polymerization comprising a metallocene supported on an inorganic solid carrier, where a carbon atom of one of the η$^5$-cyclopentadienyl rings coordinated to the transition metal is covalently bonded to a metal atom of the inorganic solid carrier. This solid component is typically used with an organic aluminum oxy-derivative which is usually alumoxane.

Supported non-alumoxane catalysts are disclosed, for example, in EP-418044, EP-522581, WO-91/09882, WO-94/03506, WO-9403509, and WO-9407927. These describe supported catalysts obtained by combining a transition metal compound, an activator component comprising a cation capable of reacting with a transition metal compound and a bulky, labile anion capable of stabilizing the metal cation formed as a result of reaction between the metal compound and the activator component, and a catalyst support material. In EP-522581 and WO-9407927 additionally an organometal compound, typically an organoaluminum compound is employed.

EP-727443 describes an olefin polymerization catalyst obtainable by contacting a transition metal compound, an organometallic compound, and a solid catalyst component comprising a carrier and an ionized ionic compound capable of forming a stable anion on reaction with said transition metal compound, wherein said ionized ionic compound comprises a cationic component and an anionic component and said cationic component is fixed on the surface of the carrier.

WO-96/04319 describes a catalyst composition comprising a metal oxide support having covalently bound to the surface thereof directly through the oxygen atom of the metal oxide, an activator anion that is also ionically bound to a catalytically active transition metal compound.

WO-93/11172 relates to polyanionic moieties comprising a plurality of non-coordinating anionic groups pendant from and chemically bonded to a core component. The core component may be a cross-linked polystyrene or polydivinylbenzene polymeric core or a polyanionic Lewis basic core substrate reactable with a Lewis acid. The polyanionic moieties are used in a non-coordinating association with cationic transition metal compounds.

Copending application Ser. No. 08/610,647, filed Mar. 4, 1996, corresponding to WO-96/28480, describes supported catalyst components comprising a support material, an organometal compound, an activator compound comprising a cation which is capable of reacting with a transition metal compound to form a catalytically active transition metal complex and a compatible anion having up to 100 nonhydrogen atoms and containing at least one substituent comprising an active hydrogen moiety. When combined with a transition metal compound, the resulting supported catalysts are very useful addition polymerization catalysts.

It would be desirable to provide a solid catalyst and solid catalyst dispersions, and components or precursors therefor, which do not require an alumoxane component and which can be used in particle formation polymerization processes without requiring a support material.

It would also be desirable to provide a solid catalyst, including precursors therefor, which when used in a polymerization process are capable of producing polymers at good catalyst efficiencies.

It is a further object to provide a solid catalyst, including precursors therefor, which when used in a particle forming polymerization process give reduced amounts of particles of undesired size and morphology. It is yet a further object to provide a solid catalyst, including precursors therefor, which when used in a particle forming polymerization process prevents or largely removes the problem of formation of polymer deposits at reactor walls and other moving parts in the reactor.

It is yet a further object to provide a solid catalyst and polymerization process that is capable of forming polymers in the form of free flowing powder or particles.

It is another object to provide a method for making a solid catalyst without requiring recovery or purification steps.

It is a further object to provide a solid catalyst which further comprises a support material.

One or several of these objects are accomplished by the embodiments of the present invention described hereinafter.

SUMMARY OF THE INVENTION

In one aspect of the present invention there is provided a catalyst component dispersion comprising (a) an ionic compound comprising a.1) a cation and a.2) an anion having up to 100 nonhydrogen atoms and said anion containing at least one substituent comprising an active hydrogen moiety, wherein (a) is in solid form dispersed in a diluent in which (a) is insoluble or sparingly soluble.

In a further aspect the invention provides a non-supported solid catalyst comprising (a) an ionic compound comprising a.1) a cation and a.2) an anion having up to 100 nonhydrogen atoms and containing at least one substituent comprising an active hydrogen moiety, (b) a transition metal compound, and (c) an organometal compound wherein the metal is selected from the Groups 1–14 of the Periodic Table of the Elements In another aspect of the invention there is provided a supported solid catalyst comprising (a) an ionic compound comprising a.1) a cation and a.2) an anion having up to 100 nonhydrogen atoms and said anion containing at least one substituent comprising an active hydrogen moiety, (b) a transition metal compound, (c) an organometal compound wherein the metal is selected from the Groups 1–14 of the Periodic Table of the Elements, and (d) a support material, wherein the solid catalyst is obtained by combining components (a), (b), (c), and (d) in any order, and wherein during at least one step in the preparation of the solid catalyst, component (a) dissolved in a diluent in which (a) is soluble, optionally in the presence of one or more of components (b), (c), and (d) or the contact product of (a) with such one or more of (b), (c), and (d), is converted into solid form.

In yet a further aspect there is provided a method for preparing a catalyst component dispersion comprising converting a solution of an ionic compound (a) comprising a.1) a cation and a.2) an anion having up to 100 nonhydrogen atoms and said anion containing at least one substituent comprising an active hydrogen moiety, in a diluent in which (a) is soluble into a dispersion comprising component (a) in solid form dispersed in a diluent in which (a) is insoluble or sparingly soluble.

In a further aspect the present invention provides a method for preparing a solid catalyst comprising combining, in any order, (a) an ionic compound comprising a.1) a cation and a.2) an anion having up to 100 nonhydrogen atoms and said anion containing at least one substituent comprising an active hydrogen moiety, (a) a transition metal compound, (c) an organometal compound wherein the metal is selected from the Groups 1–14 of the Periodic Table of the Elements, and optionally (d) a support material, wherein during at least one step in the preparation of the solid catalyst, component (a) dissolved in a diluent in which (a) is soluble, optionally in the presence of one or more of components (b), (c), and (d) or the contact product of (a) with such one or more of (b), (c), and (d), is converted into solid form, optionally followed by recovering the solid catalyst.

In yet another aspect the invention provides a method for activating a catalyst suitable for addition polymerization wherein a substantially inactive catalyst precursor comprising (a) an ionic compound comprising a.1) a cation and a.2) an anion having up to 100 nonhydrogen atoms and said anion containing at least one substituent comprising an active hydrogen moiety, (b) a transition metal compound, and optionally (d) a support material, is contacted with (c) an organometal compound wherein the metal is selected from the Groups 1–14 of the Periodic Table of the Elements, to form an active catalyst.

According to a final aspect, the present invention provides an addition polymerization process wherein one or more addition polymerizable monomers are contacted with a solid catalyst according to the invention under addition polymerization conditions.

Surprisingly, it has been found that the ionic compound (a) can be advantageously used in a solid form dispersed in a diluent in which (a) is insoluble or sparingly soluble (the diluent in which (a) is insoluble or sparingly soluble is also referred to as "non-solvent"; the diluent in which (a) is soluble is also referred to as "solvent"). By use of the dispersed solid ionic compound (a) in association with transition metal compound (b) and organometal compound (c) an active solid particulate addition polymerization catalyst results, preferably in dispersed form. Such a solid dispersed catalyst advantageously can be used in a particle forming polymerization process, such as a slurry or gas phase polymerization process, without requiring an additional support material to produce polymer of the desired particle size and morphology. The solid dispersed catalysts of the present invention can produce polymers in the form of free flowing powder or particles, without causing substantial polymer deposits at reactor walls and other moving parts in the reactor. Free flowing ethylene based polymers and interpolymers preferably have bulk densities of at least about 0.20 g/cm$^3$, and more preferably of at least about 0.25 g/cm$^3$.

When the catalyst of the present invention includes a support material (d) the versatility of the catalyst is improved. Employing a support material allows the particle size of the solid catalyst to be varied between wider ranges.

DETAILED DESCRIPTION OF THE INVENTION

All references herein to elements or metals belonging to a certain Group refer to the Periodic Table of the Elements published and copyrighted by CRC Press, Inc., 1989. Also any reference to the Group or Groups shall be to the Group or Groups as reflected in this Periodic Table of the Elements using the IUPAC system for numbering groups.

The term "non-supported" as used in the present application means in the absence of a material which typically may be used as support or carrier in addition polymerization catalyst, more in particular as olefin addition polymerization catalyst. Conversely, the term "supported" as used in the present application means in the presence of a material which typically may be used as support or carrier in addition polymerization catalyst, more in particular as olefin addition polymerization catalyst. Where in the present application the term "solid catalyst" is used, it embraces both non-supported and supported solid catalysts, unless it follows differently from the context.

Where in the present invention a composition is defined by its starting components or starting compounds optionally in combination with certain process steps, such as for example contacting and combining steps, it is meant that the composition encompasses starting components or starting compounds but also the reaction product or reaction products of the starting components or starting compounds to the extent a reaction has taken place.

The dispersion of (a) of the present invention is preferably characterized by an average particle size of (a), as measured by laser diffraction, in the range of from 0.1 to 200 μm, more preferably in the range of from 0.5 to 50 μm. The dispersion of (a) preferably contains from 0.00001 to 10 mole of solid compound (a)/l, more preferably from 0.0001 to 1 mole/l. The particle size of the dispersion of (a) was measured using a Malvern Mastersizer particle size analyser.

Ionic compounds (a) to be used in the present invention and their methods of preparation are described in U.S. patent application Ser. No. 08/610,647, filed Mar. 4, 1996 (corresponding to WO-96/28480) which is incorporated herein by reference. The term used in the anion a.2) of the ionic compound "at least one substituent comprising an active hydrogen moiety" means in the present application a substituent comprising a hydrogen atom bonded to an oxygen, sulphur, nitrogen or phosphorous atom.

In the anion a.2), the at least one substituent comprising an active hydrogen moiety preferably corresponds to the formula

$$G_q(T-H)_r \qquad (I)$$

wherein G is a polyvalent hydrocarbon radical, the group (T—H) is a radical wherein T comprises O, S, NR, or PR, the O, S, N, or P atom of which is bonded to hydrogen atom H, wherein R is a hydrocarbyl radical, a trihydrocarbyl silyl radical, a trihydrocarbyl germyl radical, or hydrogen, H is hydrogen, q is 0 or 1, and preferably 1, and r is an integer from 1 to 3, preferably 1. Polyvalent hydrocarbon radical G has r+1 valencies, one valency being associated with a metal or metalloid of the Groups 5–15 of the Periodic Table of the Elements in the anion, the other r valencies of G being attached to r groups (T—H). Preferred examples of G include di- or trivalent hydrocarbon radicals such as: alkylene, arylene, aralkylene, or alkarylene radicals containing from 1 to 20 carbon atoms, more preferably from 2 to 12 carbon atoms. Suitable examples of divalent hydrocarbon radicals G include phenylene, biphenylene, naphthylene, methylene, ethylene, 1,3-propylene, 1,4-butylene, phenylmethylene (—C$_6$H$_4$—CH$_2$—). The polyvalent hydrocarbyl portion G may be further substituted with radicals that do not negatively impact the effect to be achieved by the present invention. Preferred examples of such non-interfering substituents are alkyl, aryl, alkyl- or aryl-substituted silyl and germyl radicals, and fluoro substituents.

The group (T—H) in the previous formula may be an —OH, —SH, —NRH, or —PRH group, wherein R preferably is a C$_{1-18}$, preferably a C$_{1-12}$, hydrocarbyl radical or hydrogen, and H is hydrogen. Preferred R groups are alkyls, cycloalkyls, aryls, arylalkyls, or alkylaryls of 1 to 18 carbon atoms, more preferably those of 1 to 12 carbon atoms. Alternatively, the group (T—H) comprises an —OH, —SH, —NRH, or —PRH group which are part of a larger functional moiety such as, for example, C(O)—OH, C(S)—OH, C(S)—SH, C(O)—SH, C(O)—NRH, C(S)—NRH, and C(O)—PRH, and C(S)—PRH. Most preferably, the group (T—H) is a hydroxy group, —OH, or an amino group, —NRH.

Very preferred substituents G$_q$(T—H) in anion a.2) include hydroxy- and amino-substituted aryl, aralkyl, alkaryl or alkyl groups, and most preferred are the hydroxyphenyls, especially the 3- and 4-hydroxyphenyl groups and 2,4-dihydroxyphenyl, hydroxytolyls, hydroxybenzyls (hydroxymethylphenyl), hydroxybiphenyls, hydroxynaphthyls, hydroxycyclohexyls, hydroxymethyls, and hydroxypropyls, and the corresponding amino-substituted groups, especially those substituted with —NRH wherein R is an alkyl or aryl radical having from 1 to 10 carbon atoms, such as for example methyl, ethyl, propyl, i-propyl, n-, i-, or t-butyl, pentyl, hexyl, heptyl, octyl, nonyl, and decyl, phenyl, benzyl, tolyl, xylyl, naphthyl, and biphenyl.

The anion a.2) may further comprise a single Group 5–15 element or a plurality of Group 5–15 elements but is preferably a single coordination complex comprising a charge-bearing metal or metalloid core. Preferred anions a.2) are those containing a single coordination complex comprising a charge-bearing metal or metalloid core carrying the at least one substituent containing an active hydrogen moiety. Suitable metals for the anions of ionic compounds (a) include, but are not limited to, aluminum, gold, platinum and the like. Suitable metalloids include, but are not limited to elements of groups 13, 14, and 15, of the periodic table of elements, preferably are, boron, phosphorus, and silicon. Ionic compounds which contain anions comprising a coordination complex containing a single boron atom and one or more substituents comprising an active hydrogen moiety are preferred. Examples of suitable anions comprising a single Group 5–15 element are disclosed in EP 277 004 and examples of those having a plurality of Group 5–15 elements are disclosed in EP 0 277 003, with the proviso that at least one of the subsituents in the anions described therein is substituted by a substituent comprising an active hydrogen moiety, preferably G$_q$(T—H)$_r$.

Preferably, anions a.2) may be represented by a single coordination complex of the following general Formula (II):

$$[M'^{m+}Q_n(G_q(T-H)_r)_z]^{d-} \qquad (II)$$

wherein:

M' is a metal or metalloid selected from Groups 5–15 of the Periodic Table of the Elements;

Q independently in each occurrence is selected from the group consisting of hydride, dihydrocarbylamido, preferably dialkylamido, halide, hydrocarbyloxide, preferably alkoxide and aryloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide;

G is a polyvalent hydrocarbon radical having r+1 valencies, and preferably a divalent hydrocarbon radical, bonded to M' and r groups (T—H);

the group (T—H) is a radical wherein T comprises O, S, NR, or PR, the O, S, N, or P atom of which is bonded to hydrogen atom H, wherein R is a hydrocarbon radical, a trihydrocarbyl silyl radical, a trihydrocarbyl germyl radical, or hydrogen;

m is an integer from 1 to 7, preferably 3;

n is an integer from 0 to 7, preferably 3;

q is an integer 0 or 1, preferably 1;

r is an integer from 1 to 3, preferably 1;

z is an integer from 1 to 8, preferably 1 or 2;

d is an integer from 1 to 7, preferably 1; and n+z−m=d.

When q is 0 and polyvalent hydrocarbon radical G is not present, T is bound to M'. Preferred boron-containing anions a.2) which are particularly useful in this invention may be represented by the following general Formula (III):

wherein:

B is boron in a valence state of 3;

z' is an integer from 1–4, preferably 1 or 2, most preferably 1;

d is 1; and

Q, G, T, H, q, and r are as defined for Formula (II). Preferably, z' is 1 or 2, q is 1, and r is 1.

Illustrative, but not limiting, examples of anions a.2) of ionic compounds to be used in the present invention are boron-containing anions such as: triphenyl(hydroxyphenyl) borate, triphenyl(2,4-dihydroxyphenyl)borate, tri(p-tolyl) (hydroxyphenyl)borate, tris-(pentafluorophenyl) (hydroxyphenyl)borate, tris-(2,4-dimethylphenyl) (hydroxyphenyl)borate, tris-(3,5-dimethylphenyl) (hydroxyphenyl)borate, tris-(3,5-di-trifluoromethyl-phenyl) (hydroxyphenyl)borate, tris(pentafluorophenyl)(2-hydroxyethyl)borate, tris(pentafluorophenyl)(4-hydroxybutyl)borate, tris(pentafluorophenyl)(4-hydroxycyclohexyl)borate, tris(pentafluorophenyl)(4-(4'-hydroxyphenyl)phenyl)borate, tris(pentafluorophenyl)(6-hydroxy-2-naphthyl)borate, and the like.

Further preferred anions a.2) include those containing two substituents containing an active hydrogen moiety, for example: diphenyldi(hydroxyphenyl)borate, diphenyldi(2, 4-dihydroxyphenyl)borate, di(p-tolyl) di(hydroxyphenyl) borate, di(pentafluorophenyl)di-(hydroxyphenyl)borate, di(2,4-dimethylphenyl) di(hydroxyphenyl)borate, di (3,5-dimethylphenyl) di(hydroxyphenyl)borate, di (3,5-di-trifluoromethylphenyl) di(hydroxyphenyl)borate, di(pentafluorophenyl) di(2-hydroxyethyl)borate, di(pentafluorophenyl) di(4-hydroxybutyl)borate, di(pentafluorophenyl) di(4-hydroxycyclohexyl)borate, di(pentafluorophenyl) di(4-(4'-hydroxyphenyl)phenyl) borate, di(pentafluorophenyl) di(6-hydroxy-2-naphthyl) borate, and the like.

Other preferred anions are those above mentioned borates wherein the hydroxy functionality is replaced by an amino NHR functionality wherein R preferably is methyl, ethyl, or t-butyl. A highly preferred anion a.2) is tris (pentafluorophenyl)(4-hydroxyphenyl) borate.

The cationic portion a.1) of the ionic compound is preferably selected from the group consisting of Bronsted acidic cations, especially ammnonium and phosphonium cations or sulfonium cations, carbonium cations, silylium cations, oxonium cations, and cationic oxidizing agents. The cations a.1) and the anions a.2) are used in such ratios as to give a neutral ionic compound.

Bronsted acidic cations may be represented by the following general formula:

(L—H)⁺ wherein:

L is a neutral Lewis base, preferably a nitrogen, phosphorus, oxygen, or sulfur containing Lewis base; and (L—H)⁺ is a Bronsted acid.

Illustrative, but not limiting, examples of Bronsted acidic cations are trihydrocarbyl- and preferably trialkyl-substituted ammonium cations such as triethylammonium, tripropylammonium, tri(n-butyl)ammonium, trimethylammonium, tri(i-butyl)ammonium, and tri(n-octyl) ammonium. Also suitable are N,N-dialkyl anilinium cations such as N,N-dimethylanilinium, N,N-diethyl-anilinium, N,N-2,4,6-pentamethylanilinium, N,N-dimethylbenzylammonium and the like; dialkylammonium cations such as di-(i-propyl)ammonium, dicyclohexylammonium and the like; and triarylphosphonium cations such as triphenylphosphonium, tri(methylphenyl)phosphonium, tri(dimethylphenyl)phosphonium, dimethylsulphonium, diethylsulphonium, and diphenylsulphonium.

In a highly preferred embodiment, the Bronsted acidic cation a.1) may be represented by the following general formula:

[L*—H]⁺, wherein:

L* is a nitrogen, oxygen, sulfur or phosphorus containing Lewis base which comprises at least one relatively long chain alkyl group. Preferably such L* groups contain from one to three $C_{10-40}$ alkyl groups with a total of from 12 to 100 carbons, more preferably two $C_{10-40}$ alkyl groups and from 21 to 90 total carbons. It is understood that the cation may comprise a mixture of alkyl groups of differing lengths. For example, one suitable cation is the protonated ammonium salt derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT. These preferred cations are described in U.S. provisional application Ser. No. 60/014,284, filed Mar. 27, 1996, which is incorporated herein by reference. Ionic compounds (a) comprising the cation [L*—H]⁺ can be easily prepared by subjecting an ionic compound comprising the cation [L—H]⁺ and the anion a.2), as prepared in U.S. patent application Ser. No. 08/610,647, filed Mar.4, 1996 (corresponding to WO-96/28480), to a cation exchange reaction with a [L*—H]⁺ salt.

Illustrative, but not limiting examples of the highly preferred cations a.1) are tri-substituted ammonium salts such as: decyldi(methyl)ammonium, dodecyldi(methyl) ammonium, tetradecyldi(methyl)ammonium, hexaadecyldi (methyl)ammonium, octadecyldi(methyl)ammonium, eicosyldi(methyl)ammonium, methyldi(decyl)ammonium, methyldi(dodecyl)ammonium, methyldi(tetradecyl) ammonium, methyldi(hexadecyl)ammonium, methyldi (octadecyl)ammonium, methyldi(eicosyl)ammonium, tridecylammonium, tridodecylammonium, tritetradecylammonium, trihexadecylammonium, trioctadecylammonium, trieicosylammonium, decyldi(n-butyl)ammonium, dodecyldi(n-butyl)ammonium, octadecyldi(n-butyl)ammonium, N,N-didodecylanilinium, N-methyl-N-dodecylanilinium, N,N-di(octadecyl)(2,4,6-trimethylanilinium), cyclohexyldi(dodecyl)ammonium, and methyldi(dodecyl)ammonium.

Suitable similarly substituted sulfonium or phosphonium cations such as, di(decyl)sulfonium, (n-butyl) dodecylsulfonium, tridecylphosphonium, di(octadecyl) methylphosphonium, and tri(tetradecyl)phosphonium, may also be named.

Preferred ionic compounds (b) are di(octadecyl) methylammonium tris(pentafluorophenyl) (hydroxyphenyl) borate, octadecyl dimethylammonium tris (pentafluorophenyl)borate and di(octadecyl)(n-butyl) ammonium tris(pentafluorophenyl)(hydroxyphenyl)-borate, as well as the amino (—NHR) analogues of these compounds wherein the hydroxyphenyl group is replaced by the aminophenyl group.

A second type of suitable cation corresponds to the formula: ⓒ⁺, wherein ⓒ⁺ is a stable carbonium or silylium ion containing up to 30 nonhydrogen atoms. Suitable examples of cations include tropyllium, triphenylmethylium, benzene(diazonium). Silylium salts have been previously generically disclosed in J. Chem. Soc. Chem. Comm., 1993, 383–384, as well as Lambert, J. B., et. al., Organometallics, 1994, 13, 2430–2443. Preferred silylium cations are triethylsilylium, and trimethylsilylium and ether substituted adducts thereof.

Another suitable type of cation comprises a cationic oxidizing agent represented by the formula:

$$Ox^{e+}$$

wherein $Ox^{e+}$ is a cationic oxidizing agent having a charge of e+, and e is an integer from 1 to 3.

Examples of cationic oxidizing agents include: ferrocenium, hydrocarbyl-substituted ferrocenium, Ag⁺, and Pb²⁺.

According to a further aspect of the present invention there is provided a non-supported solid catalyst comprising the ionic compound (a), (b) a transition metal compound, and (c) an organometal compound wherein the metal is selected from the Groups 1–14 of the Periodic Table of the Elements. The present invention furthermore provides a supported solid catalyst comprising ionic compound (b), transition metal compound (b), organometal compound (c), and a support material (do. Suitable ionic compounds (a) have been described hereinabove. The non-supported solid catalyst are preferably dispersed in a diluent in which the solid catalyst is insoluble or sparingly soluble.

Suitable transition metal compounds (b) for use in the present invention include any compound or complex of a metal of Groups 3–10 of the Periodic Table of the Elements capable of being activated to olefin insertion and polymerization when combined with components (a) and (c) and optionally (d) of the present invention. Examples include Group 10 transition metal diimine derivatives which are described in WO96/23010.

Additional catalysts include derivatives of Group 3, 4, 5, or 6 or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized n-bonded ligand groups. Exemplary of such π-bonded ligand groups are conjugated or nonconjugated, cyclic or non-cyclic dienyl groups, allyl groups, boratabenzene groups, and arene groups. By the term "π-bonded" is meant that the ligand group is bonded to the transition metal by means of delocalized π electrons thereof.

Each atom in the delocalized π-bonded group may independently be substituted with a radical selected from the group consisting of hydrogen, halogen, hydrocarbyl, halohydrocarbyl, hydrocarbyl substituted metalloids, hdyrocarbyloxy, dihydrocarbylamino, wherein the metalloid is selected from Group 14 of the Periodic Table of the Elements and hydrocarbyl radicals or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, a hydrogenated fused ring system, or a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Such hydrocarbyl and hydrocarbyl-substituted organometalloid radicals may be further substituted with a Group 15 or 16 hetero-atom containing moiety. Examples of Group 15 or 16 hetero atom containing moieties include amine, phosphine, ether or thioether moieties (see for example the compounds disclosed in WO-96/13529) or divalent derivatives thereof, e.g. amide, phosphide, ether or thioether groups bonded to the transition metal or Lanthanide metal, and bonded to the hydrocarbyl group or to the hydrocarbyl substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted, $C_{1-10}$ hydrocarbyl-substituted silyl substituted, $C_{1-10}$ hydrocarbyl substituted germyl derivatives thereof, and divalent derivatives of the foregoing substituents Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 14,1, 471–480 (1995). Preferred boratabenzenes correspond to the formula:

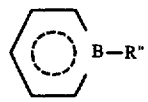

wherein R" is selected from the group consisting of hydrocarbyl, silyl, or germyl, said R" having up to 20 non-hydrogen atoms.

A suitable class of transition metal compounds useful in the present invention corresponds to the formula (V):

$$L_lMX_mX'_nX''_p, \text{ or a dimer thereof} \qquad (V)$$

wherein:

L is an anionic, delocalized, π-bonded group that is bound to M, containing up to 50 non-hydrogen atoms, optionally two L groups may be joined together forming a bridged structure, and further optionally one L may be bound to X;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral ligand base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally two X" groups may be covalently bound together to form a neutral, conjugated or nonconjugated diene that is π-bonded to M, or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two L groups. The latter complexes include those containing a bridging group linking the two L groups. Preferred bridging groups are those corresponding to the formula $(ER^*_2)_x$ wherein E is silicon, germanium, tin, or carbon, $R^*$ independently each occurrence is hydrogen or a group selected from silyl, hydrocarbyl, hydrocarbyloxy, and combinations thereof, said $R^*$ having up to 30 carbon or silicon atoms, and x is 1 to 8. Preferably, $R^*$ independently each occurrence is methyl, ethyl, propyl, benzyl, tert-butyl, phenyl, methoxy, ethoxy or phenoxy.

Examples of the complexes containing two L groups are compounds corresponding to the formula (VI) and (VII):

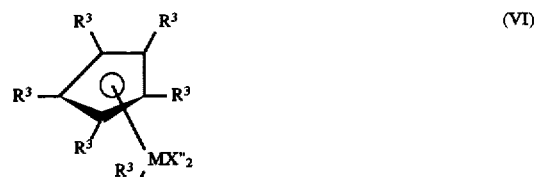

(VI)

or

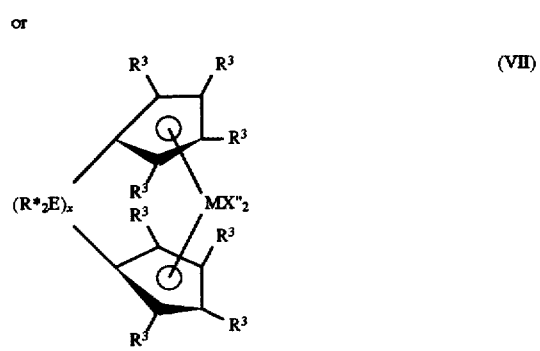

(VII)

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (i.e., a hydrocarbadiyl, siladiyl or germadiyl group) thereby forming a fused ring system, and X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and $R^*$, E and x are as previously defined for bridging groups $(ER^*_2)_x$.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., J. Am. Chem. Soc. 110, 6255–6256 (1980). Examples of chiral structures include rac bis-indenyl complexes. Similar systems based on Ti(IV) or Zr(IV) were disclosed for preparation of isotactic olefin polymers in Wild et al., J. Organomet. Chem., 232, 233–47, (1982).

Exemplary bridged ligands containing two π-bonded groups are: (dimethylsilyl-bis(cyclopentadienyl)), (dimethylsilyl-bis(methylcyclopentadienyl)), (dimethylsilyl-bis(ethylcyclopentadienyl)), (dimethylsilyl-bis(t-butylcyclopentadienyl)), (dimethylsilyl-bis(tetramethylcyclopentadienyl)), (dimethylsilyl-bis(indenyl)), (dimethylsilyl-bis(tetrahydroindenyl)), (dimethylsilyl-bis(fluorenyl)), (dimethylsilyl-bis(tetrahydrofluorenyl)), (dimethylsilyl-bis(2-methyl-4-phenylindenyl)), (dimethylsilyl-bis(2-methylindenyl)), (dimethylsilyl-cyclopentadienylfluorenyl), (dimethylsilyl-cyclopentadienyloctahydrofluorenyl), (dimethylsilyl-cyclopentadienyltetrahydrofluorenyl), (1,1,2,2-tetramethyl-1,2-disilyl-bis-cyclopentadienyl), (1,2-bis(cyclopentadienyl)ethane, and (isopropylidene-cyclopentadienyl-fluorenyl).

Preferred X" groups in formula (VI) and (VII) are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula (V) $L_lMX_mX'_nX''_p$, or a dimer thereof, wherein X is a divalent substituent of up to 50 non-hydrogen atoms that together with L forms a metallocycle with M.

Preferred divalent X substituents include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula (VIII):

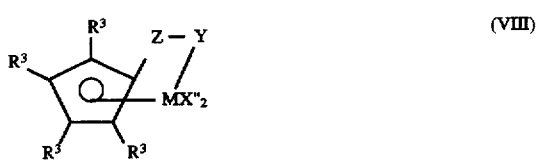

(VIII)

wherein:

M is titanium or zirconium, preferably titanium in the +2, +3, or +4 formal oxidation state;

$R^3$ in each occurrence independently is selected from the group consisting of hydrogen, hydrocarbyl, silyl, germyl, cyano, halo, hydrocarbyloxy, dihydrocarbylamino, and combinations thereof, said $R^3$ having up to 20 non-hydrogen atoms, or adjacent $R^3$ groups together form a divalent derivative (i.e., a hydrocarbadiyl, siladiyl or germadiyl group) thereby forming a fused ring system, each X' in formula (VIII) is a hydride, halide, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*—, —PR*—, —NR*$_2$ or —PR*$_2$; and

Z is SiR*$_2$, CR*$_2$, SiR*$_2$SiR*$_2$, CR*$_2$CR*$_2$, CR*=CR*, CR*$_2$SiR*$_2$, or GeR*$_2$, wherein R* is as previously defined.

Specific examples of the transition metal compounds of the types described above can be found in EP 0 129 368, EP 0 277 004, EP 0 416 815, WO-93/19104, WO-95/00526, WO-96/00734, WO-96/04290, WO-96/08498.

Suitable organometal compounds (c) for use in the present invention are those comprising metals of Groups 1–14. Component (c) contains at least one substituent selected from hydride, hydrocarbyl radicals, trihydrocarbyl silyl radicals, and trihydrocarbyl germyl radicals. Additional substituents preferably comprise one or more substituents selected from hydride, halide, hydrocarbyloxide, dihydrocarbylamide hydrocarbyl radicals, trihydrocarbyl substituted silyl radicals, trihydrocarbyl substituted germyl radicals, and hydrocarbyl-, trihydrocarbyl silyl- or trihydrocarbyl germyl-substituted metalloid radicals.

Examples of organometal compounds (c) include organo lithium, organomagnesium, organozinc, organoboron, organoaluminum, organosilicon, organogermanium, organotin, and organolead compounds, and mixtures thereof. Preferred examples are compounds represented by the following formulae: $MgR^1{}_2$, $ZnR^1{}_2$, $BR^1{}_xR^2y$, $AlR^1{}_xR^2y$, wherein $R^1$ independently each occurrence is hydride, a hydrocarbyl radical, a trihydrocarbyl silyl radical, a trihydrocarbyl germyl radical, or a trihydrocarbyl-, trihydrocarbyl silyl-, or trihydrocarbyl germyl-substituted metalloid radical, $R^2$ independently is the same as $R^1$, x is 2 or 3, y is 0 or 1 and the sum of x and y is 3, and mixtures thereof. Examples of suitable hydrocarbyl moieties are those having from 1 to 20 carbon atoms in the hydrocarbyl portion thereof, such as alkyl, aryl, alkaryl, or aralkyl. Preferred radicals include methyl, ethyl, n- or i-propyl, n-, s- or t-butyl, phenyl, and benzyl. Preferred components (c) are the aluminum compounds. Preferably, the aluminum component is an aluminum compounds of the formula $AlR^1{}_x$, wherein $R^1$ in each occurrence independently is hydride or a hydrocarbyl radical having from 1 to 20 carbon atoms, and x is 3. Suitable trihydrocarbyl aluminum compounds are trialkyl or triaryl aluminum compounds wherein each alkyl or aryl group has from 1 to 10 carbon atoms, or mixtures thereof, and preferably trialkyl aluminum compounds such as trimethyl, triethyl, tri-isobutyl aluminum.

Alumoxanes (also referred to as aluminoxanes) may also be used as component (c). Alumoxanes are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (—Al(R)—O)$_m$, for a cyclic alumoxane, and R$_2$Al—O(—Al(R)—O)$_m$—AlR$_2$, for a linear compound, wherein R independently in each occurrence is a $C_1$–$C_{10}$ hydrocarbyl, preferably alkyl, or halide and m is an integer ranging from 1 to about 50, preferably at least about 4. Alumoxanes are typically the reaction products of water and an aluminum alkyl, which in addition to an alkyl group may contain halide or alkoxide groups. Reacting several different aluminum alkyl compounds, such as, for example, trimethyl aluminum and tri-isobutyl aluminum, with water yields so-called modified or mixed alumoxanes. Preferred alumoxanes are methylalumoxane and methylalumoxane modified with minor amounts of other lower alkyl groups such as isobutyl. Alumoxanes generally contain minor to substantial amounts of starting aluminum alkyl compound.

The way in which the alumoxane is prepared is not critical. When prepared by the reaction between water and aluminum alkyl, the water may be combined with the aluminum alkyl in various forms, such as liquid, vapor, or solid, for example in the form of crystallization water. Particular techniques for the preparation of alumoxane type compounds by contacting an aluminum alkyl compound with an inorganic salt containing water of crystallization are disclosed in U.S. Pat. No. 4,542,199. In a particular preferred embodiment an aluminum alkyl compound is contacted with a regeneratable water-containing substance such as hydrated alumina, silica or other substance. This is disclosed in European Patent Application No. 338,044.

According to a further aspect the invention provides a supported solid catalyst comprising (a), (b), and (c) as described hereinbefore, as well as (d) a support material.

Suitable support materials (d), also referred to as carriers or carrier materials, which may optionally be used in the present invention include those support materials which are typically used in the art of supported catalysts, and more in particular the art of supported olefin addition polymerization supported catalysts. Examples include porous resinous materials, for example, polyolefins such as polyethylenes and polypropylenes or copolymers of styrene-divinylbenzene, and solid inorganic oxides including oxides of Group 2, 3, 4, 13, or 14 metals, such as silica, alumina, magnesium oxide, titanium oxide, thorium oxide, as well as mixed oxides of silica. Suitable mixed oxides of silica include those of silica and one or more Group 2 or 13 metal oxides, such as silica-magnesia or silica-alumina mixed oxides. Silica, alumina, and mixed oxides of silica and one or more Group 2 or 13 metal oxides are preferred support materials. Preferred examples of such mixed oxides are the silica-aluminas. The most preferred support material is silica. The shape of the silica particles is not critical and the silica may be in granular, spherical, agglomerated, fumed or other form.

Support materials suitable for the present invention preferably have a surface area as determined by nitrogen porosimetry using the B.E.T. method from 10 to about 1000 m²/g, and preferably from about 100 to 600 m²/g. The pore volume of the support, as determined by nitrogen adsorption, is typically up to 5 cm³/g, advantageously between 0.1 and 3 cm³/g, preferably from about 0.2 to 2 cm³/g. The average particle size is not critical but typically is from 0.5 to 500 μm, preferably from 1 to 200 μm, more preferably to 100 μm.

The support material may be subjected to a heat treatment and/or chemical treatment to reduce the water content or the hydroxyl content of the support material. Both dehydrated support materials and support materials containing small amounts of water can be used. Typical, chemical dehydration or dehydroxylation agents are reactive metal hydrides, alkyls and halides such as aluminum alkyls, alkyl silicon halides and the like. Prior to its use, the support material can be subjected to a thermal treatment at 100° C. to 1000° C., preferably at about 200° C. to about 850° C. in an inert atmosphere or under reduced pressure. Typically, this treatment is carried out for about 10 minutes to about 72 hours, preferably from about 0.5 hours to 24 hours.

The support material, optionally thermally treated, may preferably be combined with a further organometal compound, more preferably an organoaluminum compound, most preferably a trialkylaluminum compound in a suitable diluent or solvent, preferably one in which the organometal compound is soluble. Typical solvents are hydrocarbon solvents having from 5 to 12 carbon atoms, preferably aromatic solvents such as toluene and xylenes, or aliphatic solvents of 6 to 10 carbon atoms, such as hexane, heptane, octane, nonane, decane, and isomers thereof, cycloaliphatic solvents of 6 to 12 carbon atoms such as cyclohexane, or mixtures of any of these.

The support material is combined with the organometal compound at a temperature of −20° C. to 150° C., preferably at 20° C. to 100° C. The contact time is not critical and can vary from 5 minutes to 72 hours, and is preferably from 0.5 hours to 36 hours. Agitation is preferably applied.

An alternative pretreatment of the support material involves a treatment with alumoxane. The alumoxane may be contacted with the support material in the manner described above or the alumoxane may be generated in situ on the support material by contacting an alkylaluminum, preferably trialkylaluminum compound, with a support material containing water.

The pretreated support material is preferably recovered prior to its further use.

According to the present invention, the ionic compound (a) can be formed into a dispersion of solid particles (a) by a controlled precipitation. This dispersion can be used as such in the preparation of a solid catalyst suitable for addition polymerization processes, thereby maintaining the dispersed nature. A range of suitable particle sizes for the solid dispersed catalyst can be obtained by selecting the solvents and non-solvents, temperature conditions and the specific catalyst components. No intermediate recovery or separation steps are required and the final solid catalyst, preferably still in dispersed form, may be employed as such in an addition polymerization process. Alternatively, the particulate solid (a) and the solid catalyst, and any solid intermediate product, can be recovered from the diluent in which it is dispersed by removing the liquid or non-solvent employing techniques such as filtration, vacuum drying, spray drying, and combinations thereof. Prior to its use, the particulate solid (a), the solid catalyst, and any solid intermediate product, may be redispersed in a suitable liquid diluent.

The catalyst component dispersion of the present invention can be prepared by converting a solution of the ionic compound (a), in a diluent (solvent) in which (a) is soluble, into a dispersion comprising component (a) in solid form.

A solution of ionic compound (a) in a diluent can be obtained by using an appropriate solvent in which (a) is soluble. The diluent in which (a) is dissolved is not critical. Preferably, the diluent is compatible with the other catalyst components and under polymerization conditions, so that it does not need to be removed prior to its further use. Suitable solvents for (a) include aromatic hydrocarbons, such as toluene, benzene, ethylbenzene, propylbenzene, butylbenzene, xylenes, chlorobenzene, and the like.

When a solvent is used in which (a) is not sufficiently soluble, or in order to assist in or speed up dissolution of (a), heating may be applied or solubilizing agents may be used, or a combination of both. The solubilizing agent to be used is compatible with the catalyst components, in a sense that it does not adversely affect the beneficial properties of the catalyst. Heating is preferably done at temperatures not higher than the decomposition temperature of (a). During the dissolution of (a) stirring is advantageously applied.

Preferably, the solution of (a) contains from 0.0001 to 100 mole of (a) per liter, more preferably from 0.001 to 10 mole per liter. Any non-dissolved (a) is preferably removed by, for example, filtration techniques, prior to further using the solution of (a).

The solution of (a) is then converted into a dispersion comprising (a) in solid form. The conversion of the solution of (a) to a dispersion of (a) can be carried out, for example, by cooling the solution, by contacting the solution with a diluent (non-solvent) in which (a) is insoluble or sparingly soluble, by evaporating part of the solvent, by adding precipitating agents, or a combination of any of these techniques, to achieve a controlled precipitation or solidification such that a dispersion of (a) is formed. It will be clear to a person skilled in the art that the distinction between a solvent and a non-solvent for a particular ionic compound (a) will primarily depend on the nature of the particular compound (a), on the temperature, and relative amount of (a) to be dissolved. For a given ionic compound (a), the skilled person can easily determine what solvent and temperature conditions are to be used to obtain a solution of the desired concentration. On the other hand, given the solution of (a), the skilled person can easily determine the conditions and means to obtain the dispersion of (a) having the desired solids concentration.

When precipitating agents are used, they are preferably compatible with the catalyst components, such that the beneficial properties of the catalyst are not adversely affected.

The non-solvent employed for generating the dispersion of (a) is not critical. Preferably, the non-solvent is compatible with the other catalyst components and under polymerization conditions, so that it does not need to be removed prior to further use. Preferred non-solvents are, for example, pentane, hexane, heptane, decane, dodecane, kerosene, and higher aliphatic hydrocarbons of up to 30 carbon atoms.

The dispersion comprising component (a) is preferably generated by contacting a solution of (a) in a diluent in which (a) is soluble with a diluent in which (a) is insoluble or sparingly soluble. The diluent in which (a) is soluble is preferably selected from the group consisting of toluene, benzene, and xylenes, and the diluent in which (a) is insoluble or sparingly soluble is preferably selected from the group consisting of pentane, hexane, heptane, and octane.

In contacting the solution of (a) with the non-solvent, the amount of non-solvent is usually 10 to 10,000 parts by weight, preferably 100 to 1,000 parts by weight per 100 parts by weight of the solution of (a). The contacting temperature is usually from −100° to 300° C., preferably from −50° to 130°0C., and most preferably from 10° to 100° C.

When the solvent, in which (a) is dissolved, needs to be removed after contacting with the non-solvent, the solvent is preferably selected so that it has a lower boiling point than that of the non-solvent. The solvent can then be easily removed by heating the dispersion or by applying reduced pressure.

The solid catalysts, either supported or non-supported, according to the present invention can be prepared by combining, in any order, components (a), (b), (c), and optionally (d) in case of a supported catalyst, wherein during at least one step in the preparation of the solid catalyst, component (a) dissolved in a diluent in which (a) is soluble, optionally in the presence of one or more of components (b), (c), and (d) or the contact product of (a) with one or more of (b), (c), and (d), is converted into solid form, optionally followed by recovering the solid catalyst. After this step the other components (b), (c) and optionally (d), to the extent they have not been added before, are contacted with (a) in solid form, preferably dispersed in solid form.

According to a preferred embodiment for the preparation of the non-supported or supported solid catalyst, during the at least one step in the preparation of the solid catalyst, a dispersion comprising component (a) in solid form is generated by contacting a solution of (a) in a diluent in which (a) is soluble, optionally in the presence of one or more of components (b), (c), and (d) or the contact product of (a) with one or more of (b), (c), and (d), with a diluent in which (a) is insoluble or sparingly soluble.

In all the process steps subsequent to the dispersion formation step, it is preferred not to use temperature conditions or types or quantities of solvents that would redissolve compound (a). The methods that can be used to generate the dispersion of (a) are essentially those which have been described above in relation to the formation of the catalyst component dispersion.

In the method for preparing the non-supported or supported solid catalyst, the dispersion comprising component (a) can be formed first whereupon the other components (b), (c), and optionally (d) can be combined in arbitrary order. Further, the dispersion comprising component (a) can be formed in the presence of one or more of the other components (b), (c) and optionally (d). Exemplary embodiments are given below.

In one embodiment for preparing the non-supported or supported solid catalyst, the dispersion comprising component (a) is first contacted with component (b) and the resulting product is subsequently contacted with component (c). Component (b) is preferably employed dissolved in a suitable solvent, such as a hydrocarbon solvent, advantageously a $C_{5-10}$ aliphatic or cycloaliphatic hydrocarbon or a $C_{6-10}$ aromatic hydrocarbon. The contact temperature is not critical provided it is below the decomposition temperature of the transition metal. Component (c) can be used in a neat form, i.e. as is, or dissolved in a hydrocarbon solvent, which may be similar to the one used for dissolving component (b).

In a further embodiment for preparing the non-supported or supported solid catalyst, components (b) and (c) are first contacted, preferably in a suitable solvent, and then contacting the resulting product with the dispersion comprising component (a). The solvent or solvents used for contacting (b) and (c) are of such nature or are used in such quantities, or a combination thereof, that when the resulting product is contacted with the dispersion comprising (a), component (a) is not substantially redissolved.

In the method of preparing a supported solid catalyst, the manner in which component (d) is added is not critical. Component (d) can be added during one of the steps in the preparation of the solid catalyst. The support material (d) can be added after the components (a), (b), and (c) have been combined with each other, or (d) can be combined with at least one of the components prior to combining the resulting product with the remaining component or components.

According to a preferred embodiment for the preparation of a supported solid catalyst, component (a) dissolved in a solvent is first combined with component (d), whereupon a dispersion of (a) is generated in the manner as described above in relation to the generation of the dispersion of (a). The combining of component (d) with the solution of component (a) may be carried out while forming a slurry, i.e. using an excess amount of liquid, or alternatively, only so much of the solution of component (a) is used that no slurry is formed. Advantageously in the latter situation, the volume of the solution of component (a) does not exceed substantially, and is preferably about equal to, the pore volume of component (d). After this contacting step, component (a) is converted into solid form, preferably by combining the contact product of (a) and (d) with a diluent in which (a) is insoluble or sparingly soluble. The amount of solids relative to the amount of non-solvent is not critical but typically is from 0.001 to 50 wt. %.

When component (d) is contacted with a solution of (a), (d) is preferably used after it has been pretreated to remove substantially all water and surface hydroxyl groups, and especially by treatment with an aluminumalkyl, more preferably with an aluminumtrialkyl compound. It is advantageous to contact the solution of (a) with component (c), preferably with one molar equivalent of (c), prior to contacting the same with component (d). A highly preferred support material for use in these embodiments is pretreated silica.

Typical, yet not critical, temperatures for any of the steps except the dispersion formation step are −50° to 150° C. Preferably, each of the contacting steps is carried out while stirring or agitating. All steps in the present process should be conducted in the absence of oxygen and moisture.

The non-supported or supported solid catalyst may be stored or shipped in free flowing form under inert conditions after removal of the solvent.

The combining of components (a) and (b) in equimolar amounts does not result in a catalyst composition that has substantial activity in addition polymerization processes. Upon combining this composition with component (c) an active catalyst composition is surprisingly formed. Therefore, a further embodiment provides a method for activating a catalyst suitable for addition polymerization wherein a substantially inactive catalyst precursor comprising an ionic compound (a) and a transition metal compound (b) and optionally component (d), is contacted with organometal compound (c) to form an active catalyst. Preferably, the substantially inactive catalyst precursor is in a solid form, more preferably dispersed in a diluent.

Preferably, according to this activating method, a dispersion of a non-supported or supported solid substantially inactive catalyst precursor, comprising (a),(b) and optionally (d), and the organometal compound (c) are each separately added, preferably directly, into an addition polymerization reactor containing addition polymerizable monomer or monomers, preferably under addition polymerizable conditions. The catalyst components can be added separately to the reactor or to specific locations in the reactor which enables the catalyst to be activated only in the reactor or in a specific location in the reactor, which offers a more controllable polymerization reaction. This is especially advantageous where the addition polymerization reactor is operated under slurry phase or gas phase polymerization conditions.

The relative amounts of the components to be used in the compositions and processes of the present invention will now be described. The relative amount of ionic compound (a) to gramatoms of transition metal in compound (b), is not critical but generally is in the range from 0.1 to 500 mole of (a) per gramatoms of (b). Preferably, 0.5 to 100 mole of (a)

per gramatoms of (b) is used, most preferably from about 1 to 3 mole of (a) per gramatoms of (b).

The ratio between organometal compound (c) and the ionic compound (a) is not critical, but generally lies within the range of 0.05 to 1,000 mole of (c) per mole of (a). Preferably, the ratio is from 0.5 to 100 mole (c) per mole (a), most preferably from about 1 to 50 mole (c) per mole (a).

The amount of optional component (d) to be used in the present invention is also not critical, however, typical values range from 0.1 μmol to 2 mmol of ionic compound (a) per gram of support material. Preferably, from 10 to 1,000 μmol of ionic compound (a) is used per gram of support material.

The solid catalyst can be used as such or after being subjected to prepolymerization. The prepolymerization can be carried out by any known methods such as by bringing a small amount of one or more polymerizable monomers into contact with the solid catalyst. The monomers which can be used in the prepolymerization are not particularly limited and include the olefins and diolefins mentioned hereinafter. It is preferable to use for the prepolymerization the same monomer as used in the subsequent polymerization. The prepolymerization temperature may usually range from −20° C. to 100° C., preferably from −10° to 70° C., more preferably from 0° to 50° C., The prepolymerization may be carried out batchwise or continuously under atmospheric pressure or elevated pressures. The prepolymerization may be carried out in the presence of a molecular weight controlling agent such as hydrogen. The prepolymerization is carried out in the absence or presence of a solvent or diluent. When a solvent or diluent is used it is preferably an inert hydrocarbon, such as the ones described hereinafter with respect to the polymerization process. Preferably the solvent or diluent used does not substantially redissolve the solid catalyst comprising ionic compound (a). The prepolymerization is typically carried out to form a prepolymerized catalyst, i.e. polymer is formed on the solid catalyst particles, having from 0.1 to 100 g of polymer per 1 g of solid catalyst, preferably from 1 to 10 g of polymer per g of solid catalyst. Typical particle sizes of prepolymerized catalysts are in the range of 1 to 200 μm, preferably in the range from 10 to 100 μm.

The solid catalysts of the present invention, optionally prepolymerized, may be used in an addition polymerization process wherein one or more addition polymerizable monomers are contacted with the solid catalyst of the invention under addition polymerization conditions.

Suitable addition polymerizable monomers include ethylenically unsaturated monomers, acetylenic compounds, conjugated or non-conjugated dienes, polyenes, and carbon monoxide. Preferred monomers include olefins, for examples alpha-olefins having from 2 to about 20, preferably from about 2 to about 12, more preferably from about 2 to about 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof. Preferably, the alpha-olefins are ethylene, propene, 1-butene, 4-methyl-pentene-1, 1-pentene, 1-hexene, 1-octene, and combinations of ethylene and/or propene with one or more of such other alpha-olefins. Most preferably, ethylene or propylene is used as one of the addition polymerizable monomers. Suitable dienes include those having from 4 to 30 carbon atoms, especially those having 5 to 18 carbon atoms. Typical of these are α,ω-dienes, α-internal dienes, including those dienes which are typically used for preparing EPDM type elastomers. Typical examples include 1,3-butadiene, 1,3- and 1,4-pentadiene, 1,3-, 1,4-, and 1,5-hexadiene, 1,7-octadiene, 1,9-decadiene, and lower alkyl substituted analogues of any of these. Other preferred monomers include styrene, halo- or alkyl substituted styrenes, tetrafluoroethylene, vinylcyclobutene, dicyclopentadiene, and ethylidene norbornenes. Suitable addition polymerizable monomers include also any mixtures of the abovementioned monomers.

The solid catalyst can be formed in situ in the polymerization mixture by introducing into said mixture the catalyst components (a), (b), (c), and optionally (d).

The catalyst may be used in the polymerization reaction in a concentration of $10^{-9}$ to $10^{-3}$ moles, based on transition metal, per liter diluent or reaction volume, but is preferably used in a concentration of less than $10^{-5}$, preferably from $10^{-8}$ to $9\times10^{-6}$ moles per liter diluent or reaction volume.

The solid catalysts can be advantageously employed in a high pressure, solution, slurry, or gas phase polymerization process. A high pressure process is usually carried out at temperatures from 100° C. to 400° C. and at pressures above 500 bar. A slurry process typically uses an inert hydrocarbon diluent and temperatures of from about 0° C. up to a temperature just below the temperature at which the resulting polymer becomes substantially soluble in the inert polymerization to medium. Preferred temperatures are from about 30° C., preferably from about 60° C. to about 115° C., preferably to about 100° C. The solution process is carried out at temperatures from the temperature at which the resulting polymer is soluble in an inert solvent up to about 275° C. Generally, solubility of the polymer depends on its density. For ethylene copolymers having densities of 0.86 g/cm$^3$, solution polymerization may be achieved at temperatures as low as about 60° C. Preferably, solution polymerization temperatures range from about 75° C., more preferably from about 80° C., and typically from about 130° C. to about 260° C., more preferably to about 170° C. Most preferably, temperatures in a solution process are between about 80° C. and 150°0 C. As inert solvents typically hydrocarbons and preferably aliphatic hydrocarbons are used. The solution and slurry processes are usually carried out at pressures between about 1 to 100 bar. Typical operating conditions for gas phase polymerizations are from 20° C. to 100° C., more preferably from 40° C. to 80° C. In gas phase processes the pressure is typically from subatmospheric to 100 bar.

Preferably for use in gas phase polymerization processes, the solid catalyst has a median particle diameter from about 20 to about 200 μm, more preferably from about 30 μm to about 150 μm, and most preferably from about 50 μm to about 100 μm. Preferably for use in slurry polymerization processes, the support has a median particle diameter from about 1 μm to about 200 μm, more preferably from about 5 μm to about 100 μm, and most preferably from about 10 μm to about 80 μm. Preferably for use in solution or high pressure polymerization processes, the support has a median particle diameter from about 1 μm to about 40 μm, more preferably from about 2 μm to about 30 μm, and most preferably from about 3 μm to about 20 μm.

Further details for polymerization conditions in a gas phase polymerization process can be found in U.S. Pat. Nos. 4,588,790, 4,543,399, 5,352,749, 5,405,922, U.S. application Ser. No. 926,009, filed Aug. 5, 1992, now abandoned (corresponding to WO-94/03509), and U.S. application Ser. No. 122,852, filed Sep. 17, 1993, now abandoned (corresponding to WO-95/07942), which are incorporated herein by reference. Gas phase processes wherein condensed monomer or inert diluent is present are preferred.

In the polymerization process of the present invention impurity scavengers may be used which serve to protect the solid catalyst from catalyst poisons such as water, oxygen, and polar compounds. These scavengers can generally be used in amounts depending on the amounts of impurities. Typical scavengers include organometal compounds, and preferably trialkylaluminum or boron compounds and alumoxanes. Further, antistatic agents may be introduced into the reactor to prevent agglomeration or sticking of polymer or catalyst to the reactor walls.

In the present polymerization process also molecular weight control agents can be used, such as hydrogen or other chain transfer agents. The polymers that are prepared according to such polymerization process may be combined with any conventional additives, such as UV stabilizers, antioxidants, anti-slip or anti-blocking agents, which may be added in conventional ways, for example, downstream of the polymerization reactor, or in an extrusion or molding step.

Upon or after removal of the polymerization mixture or product of from the polymerization reactor, the supported catalyst may be deactivated by exposure to air or water, or through any other catalyst deactivating agent or procedure.

The solid catalysts of the present invention, also when used in a slurry process or gas phase process, not only are able to produce ethylene copolymers of densities typical for high density polyethylene, in the range of 0.970 to 0.940 g/cm$^3$, but surprisingly, also enable the production of copolymers having substantially lower densities. Copolymers of densities lower than 0.940 g/cm$^3$ and especially lower than 0.930 g/cm$^3$ down to 0.880 g/cm$^3$ or lower can be made while providing free flowing polymers, retaining good bulk density properties and while preventing or substantially eliminating reactor fouling. The present invention is capable of producing olefin polymers and copolymers having weight average molecular weights of more than 30,000, preferably more than 50,000, most preferably more than 100,000 up to 1,000,000 and even higher. Typical molecular weight distributions $M_w/M_n$ range from 1.5 to 15, or even higher, preferably between 2.0 and 8.0.

The solid catalysts of the present invention also can be used in a process using multiple reactors in parallel or in sequence, in combination with other catalysts, or a combination thereof.

Having described the invention the following examples are provided as further illustration thereof and are not to be construed as limiting. Unless stated to the contrary all parts and percentages are expressed on a weight basis.

EXAMPLES

The bulk density of the polymers produced in the present examples was determined according to ASTM 1895. All experiments were carried out under the exclusion of oxygen and water under a nitrogen atmosphere, unless indicated otherwise.

Preparation of the hydrochloride of Kemamine™ T9701

Kemamine™ T9701, (NMe(C$_{18}$H$_{37}$)$_2$ (13.4 gram, 25 mmol), available from Witco Corp. (Kemamine is a trademark of Witco Corp.) was dissolved in diethylether (300 ml). Hydrogen chloride gas was bubbled through the solution for 5 minutes, until the pH was acidic as shown by pH paper. The mixture was stirred for 15 minutes and the white precipitate was collected by filtration, washed with three 50 ml portions of diethylether and dried under vacuum. The yield of the NHClMe(C$_{18}$H$_{37}$)$_2$ was 12.6 gram.

Preparation of [(p-HOC$_6$H$_4$)B(C$_6$F$_5$)$_3$][NHMe(C$_{18}$H$_{37}$)$_2$]

NHClMe(C$_{18}$H$_{37}$)$_2$ (4.58 gram, 8 mmol) was dissolved in dichloromethane (50 ml). Triethylammonium tris (pentafluorophenyl)(4-hydroxyphenyl) borate [(p-HOC$_6$H$_4$)B(C$_6$F$_5$)$_3$][NHEt$_3$] (5.66 gram, 8 mmol, prepared as substantially described in Example 1B of U.S. patent application Ser. No. 08/610,647, filed Mar. 4, 1996 (corresponding to WO-96/28480)) was added followed by 40 ml distilled water. The mixture was rapidly agitated for 4 hours and then the water layer was removed by syringe. The dichloromethane layer was washed three times with 40 ml portions of distilled water. The dichloromethane layer was then dried over sodium sulphate, filtered and vacuum dried to yield an oil. The oil was extracted into toluene (200 ml), the resulting solution was filtered and the filtrate was vacuum dried to yield 8.84 gram of a colorless oil.

Preparation of catalyst 1 ml of a 0.031M solution of [(p-HOC$_6$H$_4$)B(C$_6$F$_5$)$_3$][NHMe(C$_{18}$H$_{37}$)$_2$] in toluene was treated with 18 ml of n-hexane by adding the n-hexane yielding a cloudy suspension which was stirred for 5 minutes A solution of titanium, (N-1,1-dimethylethyl)dimethyl(1-(1,2,3,4,5-eta)-2,3,4,5-tetramethyl-2,4-cyclopentadien-1-yl)silanaminato))(2-)N)-($\eta^4$-1,3-pentadiene) C$_5$Me$_4$SiMe$_2$N$^t$Bu)Ti($\eta^4$-1,3-pentadiene (0.33 ml of a 0.0925M solution in Isopar™ E; Isopar E, a trademark of Exxon Chemical Company, is a mixture of C$_8$ saturated hydrocarbons) was added to generate a red-brown colored suspension. After 5 minutes while stirring a 6 ml aliquot of this mixture was treated with 0.2 mmol of triethylaluminum (2 ml of a 0.1M solution in n-hexane) and the mixture was stirred for a further 15 minutes before using as such in a polymerization reaction.

Slurry phase polymerization

A stirred 5 l reactor was charged with 100 µmol of triisobutylaluminum, 3 l of hexane and 0.5 normal liter of hydrogen before heating to 60° C. Ethylene was then added to the reactor in an amount sufficient to bring the total pressure to 10 bar. An aliquot of the catalyst prepared as described above containing 10 µmol of titanium was then added to initiate the polymerization. The reactor pressure was kept essentially constant by continually feeding ethylene on demand during the polymerization reaction. The temperature was kept substantially constant by cooling the reactor as required. After 49 minutes the ethylene feed was shut off and the contents of the reactor were transferred to a sample pan. After drying, 925 g of a free flowing polyethylene powder was obtained. The efficiency was calculated to be 2,003,200 g polyethylene PE/g Ti and the bulk density 0.29 g/cm$^3$. Scanning electron micrographs of the polymer powder indicated the presence of spherical particles having a smooth surface morphology.

Example 2

(comparative)

The slurry polymerization procedure of Example 1 was repeated, yet without using triethylaluminum in the catalyst preparation step, without adding triisobutylaluminum to the reactor, and while using an amount of 30 µmol of titanium for the polymerization reaction. No polyethylene product was obtained.

Example 3

1 ml of a 0.031M solution of [(p-HOC$_6$H$_4$)B(C$_6$F$_5$)$_3$][NHMe(C$_{18}$H$_{37}$)$_2$] in toluene was treated with 10 ml of n-hexane yielding a cloudy suspension and the mixture was stirred for 5 minutes. A mixture of a solution of (C$_5$Me$_4$SiMe$_2$N$^t$Bu)Ti($\eta^4$-1,3-pentadiene) (0.33 ml of a 0.0925M solution in Isopar™ E) and 0.3 mmol of triethylaluminum (3 ml of a 0.1M solution in n-hexane) was added and the mixture was stirred for 15 minutes. An aliquot of this mixture containing 10 micromol of titanium was used as such in a polymerization reaction.

The polymerization conditions were identical to those of Example 1 except that the duration was 48 minutes. After drying, 850 gram of a free flowing polyethylene powder was obtained. The efficiency was calculated to be 1,774,530 g PE/g Ti.

Example 4

0.5 ml of a 0.031M solution of [(p-HOC$_6$H$_4$)B(C$_6$F$_5$)$_3$] [NHMe(C$_{18}$H$_{37}$)$_2$] in toluene was treated with 5 ml of n-hexane yielding a cloudy suspension and the mixture was stirred for 5 minutes. 0.075 mmol of triethylaluminum (0.75 ml of a 0.1M solution in n-hexane) was added and the mixture was stirred for 5 minutes. A solution of (C$_5$Me$_4$SiMe$_2$N$^t$Bu)Ti($\eta^4$-1,3-pentadiene) (0.16 ml of a 0.0925M solution in Isopar™ E) was added and the mixture stirred for 5 minutes. This mixture was used as such in a polymerization reaction.

The polymerization conditions were identical to those of Example 1 except that the duration was 30 minutes. After drying, 630 gram of a free flowing polyethylene powder was obtained. The efficiency was calculated to be 888,675 g PE/g Ti.

Example 5

40 gram of silica SP12 (Grace Davison) which had been heated at 250° C. for 3 hours under vacuum was slurried in toluene (400 ml) and then treated with 40 ml of triethylaluminum in 250 ml toluene. The mixture was stirred for 1 hour, filtered and the treated silica was washed with toluene (100 ml, of about 100° C.) and dried under high vacuum.

10 ml of a 0.031M solution of [(p-HOC$_6$H$_4$)B(C$_6$F$_5$)$_3$] [NHMe(C$_{18}$H$_{37}$)$_2$] in toluene was treated with 40 ml of n-hexane yielding a cloudy suspension. The mixture was stirred for 5 minutes. 3.1 mmol of triethylaluminum (15.5 ml of a 0.2M solution in n-hexane) was added and the mixture was stirred for 5 minutes. An aliquot of this suspension containing 40 µmole of the borate was treated with 40 µmole of a solution of (C$_5$Me$_4$SiMe$_2$N$^t$Bu)Ti($\eta^4$-1,3-pentadiene) (0.43 ml of a 0.0925M solution in Isopar E). The resulting suspension was added to a slurry of 1 gram of the silica treated as described above, in 20 ml of hexane. The mixture was stirred for 5 minutes and then an aliquot of the mixture containing 15 µmole of titanium was used as such in a slurry polymerization.

The polymerization conditions were identical to those of Example 1 except that the polymerization time was 30 minutes. 600 grams of a free flowing polyethylene powder was isolated of bulk density 0.31 g/cm$^3$. The efficiency was calculated to be 835,070 g PE/g Ti.

Example 6

2 gram of triethylaluminum treated silica (prepared as in Example 5) were placed in a 20 ml flask. In a separate vessel 1.23 ml of a solution of [(p-HOC$_6$H$_4$)B(C$_6$F$_5$)$_3$][NHMe(C$_{18}$H$_{37}$)$_2$] (0.065M) in toluene containing 80 micromol of the borate was diluted with a further 1 ml of toluene. 0.13 ml of a 0.6M solution of triethylaluminum in hexane was added and the mixture stirred for 10 minutes.

The borate/TEA solution, the volume of which about corresponded to the pore volume of the support material, was added to the treated support material and the mixture agitated. 8 ml of hexane was added to the dry powder to give a slurry followed by a solution of (C$_5$Me$_5$SiMe$_2$N$^t$Bu)Ti($\eta^4$-1,3-pentadiene) (0.86 ml of a 0.0925M solution in Isopar™ E) to yield a green colored supported catalyst.

The polymerization conditions were identical to those of Example 1 except that the polymerization time was 36 minutes and an aliquot of catalyst containing 15 micromol Ti was used. 260 gram of free flowing polymer powder of bulk density 0.25 g/cm$^3$ was obtained. The efficiency was 361, 860 g PE/g Ti.

What is claimed is:

1. A catalyst component dispersion comprising (a) an ionic compound comprising (a(1) a cation and (a)(2) an anion having up to 100 nonhydrogen atoms and said anion containing at least one substituent comprising an active hydrogen moiety, wherein (a) is in solid form in the absence of a support material and is dispersed in a diluent in which (a) is insoluble or sparingly soluble.

2. A catalyst component dispersion according to claim 1 characterized by an average particle size of (a), as measured by laser diffraction, in the range of from 0.1 to 200 µm.

3. A catalyst component dispersion according to claim 1 wherein the anion (a)(2) the at least one substituent comprising an active hydrogen moiety corresponds to general Formula (II)

wherein:

M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;
n is an integer from 0 to 7;
q is an integer of 0 or 1;
r is an integer from 1 to 3;
z is an integer from 1 to 8;
d is an integer from 1 to 7; and
n+z−m=d.

4. A catalyst component dispersion according to claim 3, wherein in the anon (a)(2) the at least one substituent comprising an active hydrogen moiety corresponds to the formula (I):

wherein G is a polyvalent hydrocarbon radical, the group (T—H) is a radical wherein T comprises O, S, NR, or PR, the O, S, N, or P atom of which is bonded to hydrogen atom H, wherein R is a hydrocarbyl radical, a trihydrocarbylsilyl radical, a trihydrocarbyl germyl radical or hydrogen, H is hydrogen, q is 0 or 1, and r is an integer from 1 to 3.

5. A catalyst component dispersion according to one of claims 1, 3 or 4, wherein the cation (a)(1) is selected from the group consisting of Bronsted acidic cations, carbonium cations, silylium cations, oxonium cations and cationic oxidizing agents.

6. A catalyst component dispersion according to claim 5, wherein the cation (a)(1) of ionic compound (a) is represented by the following general formula: [L*—H]⁺, wherein:

L* is a nitrogen, oxygen, sulfur or phosphorus containing Lewis base containing from one to three $C_{10-40}$ alkyl groups with a total of from 12 to 100 carbons.

7. A catalyst component dispersion according to claim 6, wherein the cation (a)(1) of ionic compound (a) is represented by the following general formula: [L*—H]⁺, wherein:

L* is a nitrogen, oxygen, sulfur or phosphorus containing Lewis base containing from one to three $C_{10-40}$ alkyl groups with a total of from 12 to 100 carbons, and anion (a)(2) is tris(pentafluorophenyl)(4-hydroxyphenyl) borate.

8. A method for preparing a catalyst component dispersion comprising converting a solution of an ionic compound (a) comprising (a)(1) a cation and (a)(2) an anion having up to 100 nonhydrogen atoms and said anion containing at least one substituent comprising an active hydrogen moiety, in a diluent in which (a) is soluble into a dispersion comprising component (a) in solid form in the absence of a support material.

9. The method of claim 8, wherein the dispersion comprising component (a) is generated by cooling a solution of (a) in a diluent in which (a) is soluble, by contacting a solution of (a) in a diluent in which (a) is soluble with a diluent in which (a) is insoluble or sparingly soluble, by evaporating part of the solvent, by adding precipitating agents, or a combination of any of these techniques.

10. The method of claim 9, wherein the diluent in which (a) is soluble is selected from the group consisting of toluene, benzene, and xylenes, and the diluent in which (a) is insoluble or sparingly soluble is selected from the group consisting of pentane, hexane, heptane, and octane.

11. The method of claim 8, wherein the catalyst component dispersion is characterized by an average particle size of (a), as measured by laser diffraction, in the range of from 0.1 to 200 μm.

12. The method of claim 8, wherein the anion (a)(2) corresponds to general Formula (II)

  (II)

wherein

M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—M);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;
n is an integer from 0 to 7;
q is an integer of 0 or 1;
r is an integer from 1 to 3;
z is an integer from 1 to 8;
d is an integer from 1 to 7; and
n+z—m=d.

13. The method of claim 12, wherein in the anion (a)(2) the at least one substituent comprising an active hydrogen moiety corresponds to the formula (I):

  (I)

wherein G is a polyvalent hydrocarbon radical, the group (T—H) is a radical wherein T comprises O, S, NR, or PR, the O, S, N, or P atom of which is bonded to hydrogen atom H, wherein R is a hydrocarbyl radical, a trihydrocarbylsilyl radical, a trihydrocarbyl germyl radical or hydrogen, H is hydrogen, q is 0 or 1, and r is an integer from 1 to 3.

14. The method of one of claims 8, 12 or 13, wherein the cation (a)(1) is selected from the group consisting of Bronsted acidic cations, carbonium cations, silylium cations, oxonium cations and cationic oxidizing agents.

15. The method of claim 14, wherein the cation (a)(1) of ionic compound (a) is represented by the following general formula: [L*—H]⁺, wherein:

L* is a nitrogen, oxygen, sulfur or phosphorus containing Lewis base containing from one to three $C_{10-40}$ alkyl groups with a total of from 12 to 100 carbons.

16. The method of claim 15, wherein the cation (a)(1) of ionic compound (a) is represented by the following general formula: [L*—H]⁺, wherein:

L* is a nitrogen, oxygen, sulfur or phosphorus containing Lewis base containing from one to three $C_{10-40}$ alkyl groups with a total of from 12 to 100 carbons, and anion (a)(2) is tris(pentafluorophenyl)(4-hydroxyphenyl) borate.

17. The dispersed catalyst component produced by the method of claim 8 in dry particulate form produced by removal of the solvent.

18. A method for preparing a solid nonsupported catalyst comprising combining, in any order, (a) an ionic compound comprising (a)(1) a cation and (a)(2) an anion having tip to 100 nonhydrogen atoms and the anion containing at least one substituent comprising a moiety having an active hydrogen, (b) a transition metal compound, (c) an organo-metal or metalloid compound wherein the metal or metalloid is selected from the Groups 1–14 of the Periodic Table of the Elements, wherein during at least one step in the preparation of the solid catalyst, component (a) is dissolved in a diluent in which (a) is soluble to produce a solution of (a), optionally in the presence of one or more of components (b) and (c), or the contact product of (a) with such one or more of (b) and (c), and then is converted into solid form in the absence of a support, optionally followed by recovering the solid catalyst in dry particulate form.

19. The method of claim 18, wherein the solution of (a) is produced in the presence of (b).

20. The method of claim 18, wherein the solution of (a) is produced in the presence of (c).

21. The method of claim 18, wherein the solution of (a) is produced in the presence of (b) and (c).

22. The method of claim 18, wherein during the at least one step in the preparation of the solid catalyst, a dispersion comprising component (a) in solid form is generated by cooling a solution of (a) in a diluent in which (a) is soluble, by contacting a solution of (a) in a diluent in which (a) is soluble with a diluent in which (a) is insoluble or sparingly soluble, by evaporating diluent from a solution of (a), by adding one or more precipitating agents to a solution of (a), or a combination of two or more of these techniques.

23. The method of claim 22, wherein the dispersion comprising component (a) is generated by contacting a solution of (a) in a diluent in which (a) is soluble with a diluent in which (a) is insoluble or sparingly soluble.

24. The method of claim 22, wherein the dispersion comprising component (a) is first contacted with component (b) and the resulting product is subsequently contacted with component (c).

25. The method of claim 22 wherein components (b) and (c) are contacted and the resulting product is contacted with the dispersion comprising component (a).

26. The method of claim 18, wherein the diluent in which (a) is soluble is selected from the group consisting of toluene, benzene, and xylenes, and the diluent in which (a) is insoluble or sparingly soluble is selected from the group consisting of pentane, hexane, heptane, and octane.

27. The method of claim 18, wherein the anion (a)(2) corresponds to Formula (II):

wherein:

M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H wherein R is a hydrocarbyl radical, a trihydrocarbylsilyl radical, a trihydrocarbyl germyl radical or hydrogen;

m is an integer from 1 to 7;
n is an integer from 0 to 7;
q is an integer of 0 or 1;
r is an integer from 1 to 3;
z is an integer from 1 to 8;
d is an integer from 1 to 7; and n+z−m=d.

28. The method of claim 27, wherein in the anion (a)(2) the at least one substituent comprising a moiety having an active hydrogen corresponds to Formula (I):

wherein G is a polyvalent hydrocarbon radical, the group (T—H) is a radical wherein T comprises O, S, NR, or PR, the O, S, N, or P atom of which is bonded to hydrogen atom H, wherein R is a hydrocarbyl radical, a trihydrocarbylsilyl radical, a trihydrocarbyl germyl radical or hydrogen, H is hydrogen, q is 0 or 1, and r is an integer from 1 to 3.

29. The method of claim 28, wherein the cation (a)(1) is selected from the group consisting Bronsted acidic cations, carbonium cations, silylium cations, oxonium cations, organometallic cations and cationic oxidizing agents.

30. The method of claim 29, wherein the cation (a)(1) of ionic compound (a) is represented by the following general formula: [L*—H]+, wherein:

L* is a nitrogen, oxygen, sulfur or phosphorus containing Lewis base containing from one to three $C_{10-40}$ alkyl groups with a total of from 12 to 100 carbons.

31. The method of claim 30, wherein the cation (a)(1) of ionic compound (a) is represented by the following general formula: [L*—H]+, wherein:

L* is a nitrogen, oxygen, sulfur or phosphorus containing Lewis base containing from one to three $C_{10-40}$ alkyl groups with a total of from 12 to 100 carbons, and the anion (a)(2) is tris(pentafluorophenyl)(4-hydroxyphenyl)borate.

32. The method of claim 18, wherein the catalyst is essentially free of alumoxane.

33. A solid nonsupported catalyst produced by the method of one of claims 18–32.

34. A nonsupported catalyst produced from components comprising, in the absence of a support material, (a) an ionic compound comprising (a)(1) a cation and (a)(2) an anion having up to 100 nonhydrogen atoms and the anion containing at least one substituent comprising a moiety having an active hydrogen, (b) a transition metal compound, and (c) an organometal or metalloid compound wherein the metal is selected from the Groups 1–14 of the Periodic Table of the Elements.

35. The nonsupported catalyst of claim 34, wherein the anion (a)(2) corresponds to Formula (II):

wherein:

M' is a metal or metalloid selected from Groups 5–15 of the Periodic Table of the Elements;

Q independently in each occurrence is selected from the group consisting of hydride, dihydrocarbylamido, halide, hydrocarbyloxide, hydrocarbyl, and substituted-hydrocarbyl radicals, including halo-substituted hydrocarbyl radicals, and hydrocarbyl- and halohydrocarbyl-substituted organo-metalloid radicals, the hydrocarbyl portion in each of these groups preferably having from 1 to 20 carbons, with the proviso that in not more than one occurrence is Q halide; G is a polyvalent hydrocarbon radical having r+1 valencies bonded to M' and r groups (T—H);

the group (T—H) is a radical wherein T comprises O, S, NR, or PR, the O, S, N or P atom of which is bonded to hydrogen atom H, wherein R is a hydrocarbyl radical, a trihydrocarbylsilyl radical, a trihydrocarbyl germyl radical or hydrogen;

m is an integer from 1 to 7;
n is an integer from 0 to 7;
q is an integer of 0 or 1;
t is an integer from 1 to 3;
z is an integer from 1 to 8;
d is an integer from 1 to 7; and
n+z−m=d.

36. The nonsupported catalyst of claim 35, wherein in the anion (a)(2) the at least one substituent comprising a moiety having an active hydrogen corresponds to Formula (I):

wherein G is a polyvalent hydrocarbon radical, the group (T—H) is a radical wherein T comprises O, S, NR or PR, the O, S, N, or P atom of which is bonded to hydrogen atom H, wherein R is a hydrocarbyl radical, a trihydrocarbylsilyl radical, a trihydrocarbyl germyl radical or hydrogen, H is hydrogen, q is 0 or 1, and r is an integer from 1 to 3.

37. The nonsupported catalyst of claim 34, wherein the cation (a)(1) is selected from the group consisting of Bronsted acidic cations, carbonium cations, silylium cations, oxonium cations, organometallic cations and cationic oxidizing agents.

38. The nonsupported catalyst of claim 37, wherein the cation (a)(1) of ionic compound (a) is represented by the following general formula: $[L^*—H]^+$, wherein:

L* is a nitrogen, oxygen, sulfur or phosphorus containing Lewis base containing from one to three $C_{10-40}$ alkyl groups with a total of from 12 to 100 carbons.

39. The nonsupported catalyst of claim 38 wherein the cation (a)(1) of ionic compound (a) is represented by the following general formula: $[L^*—H]^+$, wherein:

L* is a nitrogen, oxygen, sulfur or phosphorus containing Lewis base containing from one to three $C_{10-40}$ alkyl groups with a total of from 12 to 100 carbons, and anion (a)(2) is tris(pentafluorophenyl)(4-hydroxyphenyl)borate.

40. The nonsupported catalyst of claim 34 wherein (b) is any compound or complex of a metal of Groups 3–10 of the Periodic Table of the Elements capable of being activated to olefin insertion and polymerization when combined with components (a) and (c).

41. The nonsupported catalyst of claim 40, wherein in the organometal or metalloid compound (c) the metal or metalloid is Li, Mg, Zn, B, Al, Si, Ge, Sn, or Pb.

42. The nonsupported catalyst of claim 41, wherein the organometal or metalloid compound (c) corresponds to the formula $MgR^1_2$, $ZnR^1_2$, $BR^1_xR^2_y$, or $AlR^1_xR^2_y$, wherein $R^1$ independently each occurrence is hydride, a hydrocarbyl radical, a trihydrocarbyl silyl radical, a trihydrocarbyl germyl radical, or a trihydrocarbyl-, trihydrocarbyl silyl-, or trihydrocarbyl germyl-substituted metalloid radical, $R^2$ independently is the same as $R^1$, x is 2 or 3, y is 0 or 1 and the sum of x and y is 3, and mixtures thereof.

43. The nonsupported catalyst of claim 42, wherein in the organometal or metalloid compound (c) the metal or metalloid is aluminum.

44. The nonsupported catalyst of claim 43, wherein the organometal or metalloid compound corresponds to the formula $AlR^o_x$, wherein $R^o$ independently in each occurrence is hydrogen or a hydrocarbyl radical having from 1 to 20 carbon atoms, and x is 3.

45. The nonsupported catalyst of claim 34, wherein the organometal or metalloid compound is an alumoxane or a mixture of an alumoxane with an organometal or metalloid compound of formula $AlR^o_x$, wherein $R^o$ independently in each occurrence is hydrogen or a hydrocarbyl radical having from 1 to 20 carbon atoms, and x is 3.

46. The nonsupported catalyst of claim 34 dissolved in a diluent.

47. The nonsupported catalyst of claim 34 in solid form dispersed in a diluent in which the solid catalyst is insoluble or sparingly soluble.

48. The nonsupported solid catalyst of claim 47 in dry particulate form produced by removal of the diluent.

49. The nonsupported solid catalyst of claim 48, wherein the catalyst is prepolymerized.

* * * * *

UNITED STATES PATENT AND TRADEMARK OFFICE
CERTIFICATE OF CORRECTION

PATENT NO. : 5,783,512

DATED : July 21, 1998

INVENTOR(S) : Grant B. Jacobsen et al.

It is certified that error appears in the above-identified patent and that said Letters Patent is hereby corrected as shown below:

Claim 1, column 24, line 11, "(a(1)" should correctly read --(a)(1)--.

Claim 3, column 24, line 21-22, delete "the at least one substituent comprising an active hydrogen moiety".

Claim 12, column 25, line 65, "(T—M)" should correctly read --(T—H)--.

Claim 27, column 27, line 37, delete "preferably".

Claim 35, column 28, line 45, delete "preferably".

Signed and Sealed this

Seventeenth Day of October, 2000

Attest:

Q. TODD DICKINSON

*Attesting Officer*       *Director of Patents and Trademarks*